United States Patent
Coppola et al.

(10) Patent No.: US 10,071,322 B2
(45) Date of Patent: Sep. 11, 2018

(54) HYDROTHERMAL CLEANUP PROCESS (71) Applicant: Applied Research Associates, Inc., Albuquerque, NM (US)

(72) Inventors: Edward N. Coppola, Panama City, FL (US); Charles Red, Jr., Youngstown, FL (US); Sanjay Nana, Panama City, FL (US)

(73) Assignee: Applied Research Associates, Inc., Albuquerque, NM (US)

( * ) Notice: Subject to any disclaimer, the term of this patent is extended or adjusted under 35 U.S.C. 154(b) by 234 days.

(21) Appl. No.: 15/007,658

(22) Filed: Jan. 27, 2016

(65) Prior Publication Data

US 2016/0214028 A1    Jul. 28, 2016

Related U.S. Application Data (60) Provisional application No. 62/108,770, filed on Jan. 28, 2015.

(51) Int. Cl.
*B01D 17/02* (2006.01)
*B01D 3/00* (2006.01)
(Continued)

(52) U.S. Cl.
CPC .............. *B01D 11/04* (2013.01); *B01D 3/009* (2013.01); *B01D 17/0214* (2013.01); *C07C 7/04* (2013.01);
(Continued)

(58) Field of Classification Search
CPC . B01D 11/04; B01D 11/0403; B01D 11/0488; B01D 11/0492; B01D 3/00;
(Continued)

(56) References Cited

U.S. PATENT DOCUMENTS 5,492,634 A * 2/1996 Hong ............... B01J 3/008 210/758
6,066,263 A * 5/2000 Makino ............ B01J 3/04 210/177

(Continued)

FOREIGN PATENT DOCUMENTS

WO    2015094948 A1    6/2015

OTHER PUBLICATIONS

King et al., "Hydrolysis of soybean oil in a subcritical flow reactor", Green Chemistry, 1999, p. 261-264, The Royal Society of Chemistry 1999.

*Primary Examiner* — Joseph W Drodge
(74) *Attorney, Agent, or Firm* — The Webb Law Firm (57) ABSTRACT A high-rate hydrothermal cleanup (HCU) process and system is disclosed for the rapid hydrolysis of renewable oils and reduction of inorganic and organic contaminants, such as salts, minerals, metals, asphaltenes, polymers, and coke precursors in both renewable oils and petroleum fractions. The process and system is characterized by a very short residence time, high-temperature, high-pressure, turbulent flow, hydrothermal operation. The HCU and integrated vapor-liquid separation system and process results in high yields of oil product that contains significantly reduced concentrations of inorganic and organic contaminants. The process may be operated to produce a concentrated clean glycerin byproduct and short-chain and long-chain free fatty acid product streams. The integrated vapor-liquid separation system and process performs at near atmospheric pressure by taking advantage of the water employed in the cleanup process and the energy imparted by the HCU reactor and eliminates the need for vacuum distillation.

20 Claims, 2 Drawing Sheets

(51) Int. Cl.
  *B01D 11/04* (2006.01)
  *C10G 31/06* (2006.01)
  *C10G 31/08* (2006.01)
  *C07C 7/04* (2006.01)
  *C07C 7/08* (2006.01)
(52) U.S. Cl.
  CPC ............... *C07C 7/08* (2013.01); *C10G 31/06* (2013.01); *C10G 31/08* (2013.01)
(58) Field of Classification Search
  CPC ........ B01D 3/009; B01D 5/00; B01D 5/0003; B01D 5/0057; B01D 5/006; B01D 5/0069; B01D 5/0075; B01D 5/009; B01D 17/02; B01D 17/0208; B01D 17/0214; B01D 17/04; B01D 17/12; B01D 19/00; B01D 19/0005; B01D 19/001; B01D 19/0068; B01D 19/0073; C07C 7/00; C07C 7/005; C07C 7/04; C07C 7/05; C07C 7/08; C07C 7/10; C10G 7/00; C10G 7/04; C10G 31/08; C10G 33/00; C10G 33/06; C10G 31/06; C11B 1/00; C11B 1/10; C11B 1/104; C11B 1/108; C11B 9/02; C11B 9/025; C11B 9/027; C11B 3/006; C11B 3/02; C11B 3/12; C11B 3/14
  USPC .... 95/241, 243, 251, 254, 263, 264; 96/182, 96/218; 202/82, 152, 158, 159, 176, 177, 202/182, 197; 203/28, 39; 208/184, 187; 210/634, 774, 800, 804, 806, 180, 182, 210/259, 908, 909; 554/175; 585/802, 585/833
  See application file for complete search history.

(56) References Cited

U.S. PATENT DOCUMENTS

| | | | |
|---|---|---|---|
| 6,399,802 B2 | 6/2002 | Reaney | |
| 6,475,396 B1* | 11/2002 | Wofford, III | B01J 19/26 210/198.1 |
| 6,506,308 B1* | 1/2003 | Rolf | C02F 1/5236 210/691 |
| 7,399,408 B2* | 7/2008 | Joussot-Dubien | A62D 3/20 210/179 |
| 7,691,159 B2 | 4/2010 | Li | |
| 8,815,081 B2* | 8/2014 | Choi | C10G 9/00 208/107 |
| 9,024,096 B2 | 5/2015 | Greene | |
| 9,162,938 B2 | 10/2015 | Mukherjee et al. | |
| 2003/0045655 A1* | 3/2003 | Hendriksen | C07C 7/005 526/77 |
| 2004/0129646 A1 | 7/2004 | Conaway et al. | |
| 2007/0056881 A1 | 3/2007 | Berkowitz et al. | |
| 2009/0166262 A1 | 7/2009 | He et al. | |
| 2010/0028236 A1* | 2/2010 | Shen | B01J 19/1806 423/263 |
| 2011/0252696 A1* | 10/2011 | Franklin | C11B 1/06 44/388 |
| 2011/0315600 A1 | 12/2011 | Choi et al. | |
| 2012/0073184 A1* | 3/2012 | Cranford | C11B 1/02 44/307 |
| 2012/0190872 A1* | 7/2012 | Cranford | C11B 1/02 554/207 |
| 2013/0134351 A1* | 5/2013 | Bathurst | B01D 11/0426 252/183.13 |
| 2013/0137154 A1* | 5/2013 | Reep | C10L 1/02 435/168 |
| 2014/0109465 A1* | 4/2014 | Coppola | B01J 19/2405 44/307 |
| 2014/0251871 A1 | 9/2014 | Choi et al. | |
| 2014/0305031 A1* | 10/2014 | Day | C12P 7/6418 44/388 |
| 2015/0126758 A1* | 5/2015 | Elliott | C10G 33/06 554/23 |
| 2015/0152336 A1 | 6/2015 | Greene | |
| 2015/0203768 A1* | 7/2015 | Coppola | C10G 55/04 208/86 |
| 2015/0217265 A1 | 8/2015 | Greene | |
| 2015/0329788 A1 | 11/2015 | Greene | |

\* cited by examiner

HYDROTHERMAL CLEANUP PROCESS

CROSS REFERENCE TO RELATED APPLICATIONS

This application claims benefit of priority from U.S. Provisional Patent Application No. 62/108,770, filed Jan. 28, 2015, which is incorporated herein by reference in its entirety.

FIELD OF THE INVENTION

The present invention is directed to a hydrothermal cleanup (HCU) process and system for the rapid hydrolysis of renewable oils and reduction of inorganic and organic contaminants, such as salts, minerals, metals, asphaltenes, and coke precursors in both renewable oils and petroleum fractions. The process and system is characterized by a very short residence time, high-temperature, high-pressure, turbulent flow, hydrothermal operation.

BACKGROUND OF THE INVENTION

The ever-increasing demand for renewable fuels and chemicals has forced refineries to look to alternative hydrocarbon sources and ways to upgrade and convert these sources or feedstocks into viable products. In particular, refineries need processes to upgrade renewable and non-renewable feedstocks, such as plant oils, algal and microbial oils, waste vegetable oils, yellow and brown grease, tallow, soap stock, pyrolysis oils from plastics or cellulose, and petroleum fractions into high-value, light- and middle-distillate hydrocarbon products. Renewable, waste, and low-cost feedstocks often contain contaminants that must be removed collectively prior to upgrading by conventional refinery processes into clean hydrocarbon fuels or chemicals.

Renewable plant oils typically contain phospholipid compounds or complexes, referred to herein as phospholipids. The phosphorous in phospholipids creates two primary problems for conventional refinery unit operations. First, phosphorus is a nucleating site and catalyst for coke formation. Renewable and petroleum feedstocks that are high in phosphorus cause coking in fired-furnaces and heat exchangers, which greatly increases downtime for decoking and other maintenance operations. Second, phosphorus irreversibly poisons and deactivates catalysts used in hydrotreating, hydrocracking, and hydroisomerization, leading to more frequent and costly catalyst replacement. Catalysts may be protected using guard beds containing alumina or similar high-surface area materials that can sorb low concentrations of metal and phosphorus compounds, but this approach is cost prohibitive for renewable oils containing high levels of phospholipids.

Renewable oils containing phospholipids may be chemically degummed to eliminate phosphorus. Phospholipids contain a diglyceride (two fatty acid chains covalently bonded to a glycerin molecule through ester linkages), a phosphate group ($PO_4^{3-}$), and are typically complexed with various organic molecules, such as choline ($C_5H_{14}NO$), ethanolamine, serine, inositol, and the like. Conventional chemical degumming uses phosphoric acid or citric acid to remove phosphorus as phosphatidic acid. Phosphatidic acid includes the two fatty acids and the glycerin backbone from the original, phospholipid. Thus, conventional chemical degumming of a plant or algal oil that is high in phospholipid content results in significant yield loss because the entire phospholipid diglyceride is removed from the treated oil.

Processes for converting renewable oils into renewable, hydrocarbon fuels (as opposed to fatty acid methyl esters or FAME biodiesel) typically hydrotreat the triglyceride feedstock resulting in hydrogenolysis of the glycerin backbone. Partially due to the hydrogen that is required to hydrotreat the glycerin backbone, which produces propane (a low-value byproduct), this process requires up to 100% more hydrogen than is required for fatty acid deoxygenation alone. Hydrolysis or "fat-splitting" processes may be used to produce glycerin and free fatty acids that are used for renewable fuel or chemical production. A widely employed hydrolysis process is the Colgate-Emery process.

The Colgate-Emery process is a continuous-flow, counter-current process that typically operates at 250-260° C. and 725 psig. Oil is fed into the bottom of a splitting tower and demineralized water is fed into the top of the tower. Fatty acids are discharged from the top of the tower and a water-glycerin solution (sweet water) is removed from the bottom of the tower. Processing time is 2 to 3 hours, which requires very large heated pressure vessels for large commercial applications. Several factors limit the performance of a Colgate-Emery process: 1) the need to operate below the glycerin decomposition temperature, which is approximately 290° C.; 2) the need to provide long residence time for hydrolysis and to permit gravity separation of free fatty acid and glycerin-water phases; and 3) the economical tradeoff between operating temperature, pressure, and residence time. Operation of the Colgate-Emery process at higher temperature requires higher pressure and risks decomposition of glycerin due to the long residence time at temperatures near 290° C. The large equipment required makes this process cost prohibitive for alternative fuel production due to the large volumes of oil that must be processed in order to achieve economic viability. Sweet water (a diluted solution of glycerin) may form an emulsion due to the presence of residual free fatty acids and partially hydrolyzed triglycerides. To recover the dilute glycerin product, sweet water typically must settle for up to 24 hours at 80-90° C. with demulsifying agents. Vacuum distillation may also be used to further separate long- and short-chain fatty acids.

Solvent deasphalting is a refinery process for extracting asphaltenes and resins from atmospheric tower bottoms (ATB) or other heavy petroleum fraction to produce deasphalted oil (DAO) that can be used as feed to fluid catalytic cracking or hydrocracking systems. The process consists of contacting the feedstock with a solvent in a counter-current extractor at temperatures and pressures to precipitate the asphaltene and resin fractions that are not soluble in the solvent. Solvents may be low molecular weight paraffins such as propane, butane, pentane, or hexane. The solvent deasphalting process requires a considerable amount of expensive solvent. Solvent recovery is an energy-intensive process. DAO yields are typically only 40-60% and higher yields can only be obtained by sacrificing DAO quality.

Salt compounds also must be limited in crude feedstocks due to corrosion, coking, and catalyst fouling issues that arise when salt compounds are present in the feedstock during feedstock conversion. Conventional desalting processes mix petroleum crude oil and water at elevated temperatures through a mixing valve to form an intimately mixed stream that is then fed to a large oil-water separator. Separation is facilitated by passing high frequency alternating current through the organic phase to cause small water droplets to coalesce. Demulsifying agents are also used to facilitate removal of water. Often, a two-stage desalting system is required. Renewable oils, such as waste vegetable oil, yellow and brown grease, and tallow, are difficult to desalt using conventional petroleum desalters, in part, due to the conductivity of these oils and their potential to form soaps and emulsions.

SUMMARY OF THE INVENTION

The present invention is directed to a process and system for the hydrothermal cleanup of renewable or non-renewable organic feedstocks, such as renewable plant oil, algal and microbial oils, waste vegetable oils, brown grease, tallow; oils from recycled petroleum products, plastics, and elastomers; and petroleum crude oil or crude oil fractions. This invention has numerous advantages over other cleanup processes such as chemical degumming, desalting processes, or other chemical, extraction, or thermal processes. Advantages include, but are not limited to: 1) equipment that exhibits a small footprint that can be co-located with a conventional refinery or implemented in the field; 2) the ability to recover valuable aqueous or organic products or byproducts; and 3) incorporation of integral high-energy atmospheric vapor-liquid separation or rectification of the product stream that eliminates the need for vacuum distillation to separate or concentrate products. The process and system of the invention results in a high product yield with significantly reduced concentrations of salts, metals, and minerals, such as silicas, oxides, carbonates, sulfates, and phosphates. The system is specifically desirable for use in processing unrefined plant oil, algal oils, waste vegetable oils, and oils from recycled plastic, elastomers, and petroleum crude oils or petroleum fractions such as atmospheric tower bottoms (ATB). At the elevated temperatures employed during hydrothermal cleanup, renewable oils and water become miscible, which results in rapid desalting and rapid separation of water and organic phases with or without demulsifying agents.

The present invention includes a process for reducing contaminants in petroleum or renewable feedstocks comprising: combining a feedstock comprising contaminants with a water feed to form a contaminated feedstock mixture; feeding the mixture into a HCU reactor, wherein the mixture is subjected to heat, pressure, and turbulent flow conditions that do not cause conversion of the feedstock, maintaining the temperature, pressure and turbulent flow conditions such that inorganic contaminants are liberated from the feedstock in the mixture without feedstock conversion; and separating an effluent from the reactor into an aqueous or organic stream and at least one product stream. The resulting product stream has a lower concentration of inorganic contaminants than in the contaminated feedstock. The HCU reactor is operated at temperatures and water concentrations that enable separation of free fatty acids (FFA) or hydrocarbon distillate at near atmospheric pressure.

The product from the HCU reactor may be cooled and separated directly into aqueous and organic phases, or depressurized and fed directly into a vapor-liquid separator system that separates water, light organic product, and contaminants from clean FFAs product. The separation system may include one or more flash, rectifying, stripping, or distillation columns, and one or more condensers.

Also included in the present invention is a hydrothermal cleanup system for decontaminating feedstock oils comprising: a high-rate hydrothermal reactor system operated at a temperature and pressure to maintain liquid, vapor-liquid, or supercritical conditions that result in complete hydrolysis and/or liberation of inorganic contaminants from a mixture of a feedstock oil and water without conversion of the feedstock; and a separation system for removing a clean product stream and water and/or oil stream containing inorganic contaminants from the effluent of the high-rate reactor system.

DESCRIPTION OF THE INVENTION

As used herein, unless otherwise expressly specified, all numbers, such as those expressing values, ranges, amounts, or percentages may be read as if prefaced by the word "about", even if the term does not expressly appear. Any numerical range recited herein is intended to include all sub-ranges subsumed therein. Plural encompasses singular and vice versa. When ranges are given, any endpoints of those ranges and/or numbers within those ranges can be combined with the scope of the present invention. "Including", "such as", "for example", and like terms mean "including/such as/for example but not limited to".

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting. Like reference numerals refer to like elements.

It should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all sub-ranges beginning with a minimum value equal to or greater than 1 and ending with a maximum value equal to or less than 10, and all sub-ranges in between, e.g., 1 to 6.3, or 5.5 to 10, or 2.7 to 6.1.

The present invention is directed to a continuous-flow process and system for the hydrothermal cleanup of renewable or non-renewable organic feedstocks, such as renewable plant oil, algal and microbial oils, waste vegetable oils, brown grease, tallow; oils from recycled petroleum products, plastic, and elastomers; and petroleum crude oil or crude oil fractions. The process of the present invention separates undesirable contaminants such as minerals, metals, salts, and asphaltenes, from the feedstock to produce clean oil. By "clean" it is meant that contaminants in the product have been reduced by greater than 95%, such as by more than 99%, often resulting in trace amounts (near or below typical analytical method detection limits) of contaminants compared to the feedstock. The level of contaminants in the clean oil is minimized to greatly reduce deposition, polymerization, and coking in downstream conversion equipment and deactivation or fouling of downstream conversion catalysts. The cleanup process is accomplished by hydrolysis, solvation, stripping, suspension, and/or concentration of contaminants in water or a residual organic byproduct stream. The HCU process does not include conversion of the feedstock. By "conversion" it is meant molecular rearrangement of hydrocarbon structures or FFAs, such as occurs in decarboxylation, cracking, isomerization, cyclization, hydrogenation, or dehydrogenation. These conversion processes may be performed downstream of the system of the present invention, thereby benefitting from conversion of clean feedstock and reducing or eliminating the problems associated with conversion of contaminated feedstocks.

The contaminated feedstocks may be petroleum-based feedstocks, such as petroleum crude oil, shale oil, petroleum refinery intermediate streams (such as ATBs or vacuum tower bottoms (VTB)), pyrolysis oils, recycled plastics, coal liquids, used motor oil, and mixtures thereof. Alternatively, the contaminated feedstock may be renewable feedstock, such as plant oil. Suitable plant oils for treating according to the present invention include oils of canola, Carinata, castor, Jatropha, palm, Pongamia, soy bean, tung, and/or corn (such as derived from distiller grains), soap stock, waste vegetable oil, yellow grease (from cooking oil), brown grease (from grease traps and wastewater treatment), highly acidic oils (also referred to as acidic oils), animal tallow, algal oil, microbial oil, terpenes and other pine-related byproducts from tall oils, or other biosynthetic oils (such as derived from pyrolysis, esterification, oligomerization, or polymerization) and mixtures thereof. Contaminants that may be removed include inorganic materials, such as halides (e.g., Cl, Br, I) phosphorus and phosphorus-containing species, alkali metals and metalloids (e.g., B, Na, K, Si), and other metals (e.g., Ca, Fe, Mg, Ni, V, Zn). Organic contaminants for removal may include asphaltenes, polymers (such as polyesters and/or polypropylenes), high molecular weight organic compounds or waxes (such as containing more than 50-60 carbon atoms and/or having a boiling point greater than 600° C.), coke, and/or coke precursors. The process and system results in clean oil by achieving more than 95% (such as more than 99%) reduction in phosphorus, salt, mineral, and metal content. In the case of renewable oils, feedstocks containing triglycerides are rapidly hydrolyzed into FFAs. In phospholipid feedstocks, phosphorus content is reduced from thousands of parts per million (ppm) to less than 50 ppm at a fraction of the yield loss associated with conventional degumming. The system of the present invention includes a high-temperature, high-pressure, hydrothermal reactor system coupled with components for separation and/or recovery of a clean oil product with no other operations or additions therebetween. The integrated reactor and separation systems are the basis of the HCU process. The HCU process may be operated in a manner that produces a clean petroleum crude oil fraction, clean FFAs from renewable feedstocks, and/or clean distillate fractions from petroleum or renewable oils. For example, the concentration of inorganic contaminants is reduced to the degree that the resultant clean oils may be effectively upgraded using hydrothermal cracking in a high-rate reactor system or upgraded using conventional refinery hydroprocessing operations (hydrotreating, hydrocracking, and/or hydroisomerization) with reduced coke formation, reduced catalyst fouling, and reduced catalyst deactivation. Effluent streams may be recovered, recycled, or refined to recover valuable byproducts.

Figure 1:
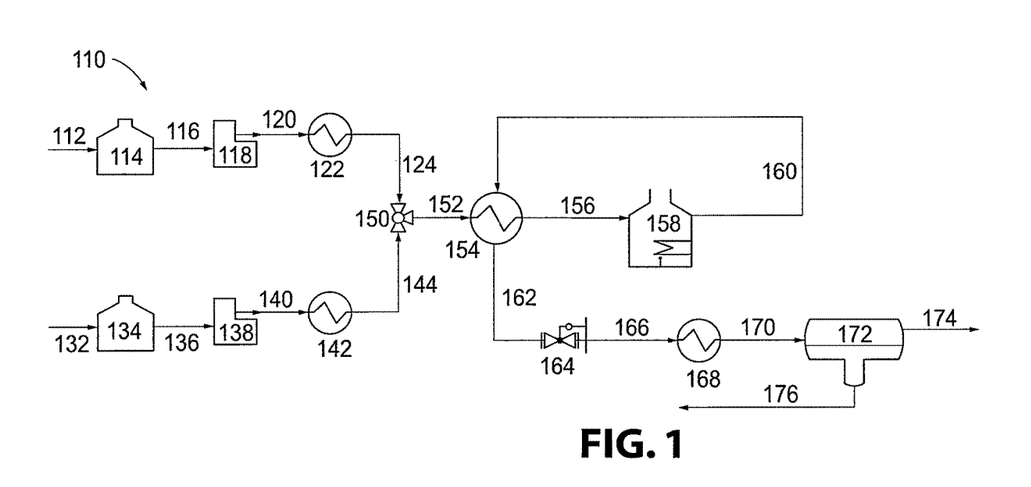
FIG. 1 is a schematic view of the HCU system in accordance with the invention for the hydrolysis and cleanup of renewable oils or petroleum-based oils where the products are recovered by conventional oil-water separation.

Reference is now made to FIG. 1, which shows a schematic view of the HCU process and system, generally indicated as 110, in accordance with an embodiment of the invention, for the hydrolysis and/or cleanup of renewable oils, including waste oils such as brown grease and yellow grease, or petroleum-based oils where the products are recovered by conventional oil-water separation. The process and system includes providing a renewable or petroleum-based contaminated feedstock 112. The contaminated feedstock 112 may be fed into an equalization tank 114. Generally, an equalization tank acts as a holding tank that allows for the equalization of flow of the feedstock. An equalization tank can also act as a conditioning operation where the temperature of the feedstock is controlled to maintain desired flow characteristics. The contaminated feedstock exits the equalization tank 114 at 116 and enters into pump 118 to form a pressurized feed stream 120. The pressurized feed stream 120 can be heated by a heating device, such as a heat exchanger 122, to form a heated feed stream 124.

A water feed stream 132 can be supplied to an equalization tank 134 and fed at 136 to a pump 138 to form a pressurized water stream 140. The pressurized water stream 140 can be heated by a heating device, such as a heat exchanger 142, to form a heated water stream 144. It should be appreciated that streams 124 and 144 can be heated by any known process or device and includes heat recovery from other process streams to optimize overall thermal efficiency.

The heated feed stream 124 and heated water stream 144 are mixed at mixing device 150 to form a high-pressure mixed stream 152. Sufficient pressure is required to maintain the feedstock and water streams in liquid, vapor-liquid, or supercritical phases at conditions necessary to accomplish cleanup based on the feedstock properties. Renewable feedstocks may become miscible with water at temperatures as low as 300° C. and pressure as low as 1,250 psig. Typical petroleum feedstocks require supercritical conditions to become miscible with water, namely greater than 372° C. and over 3,200 psig. It can be appreciated that the mixing device 150 may be a combination of the two streams via a tee connection or may include one or more conventional static mixers, mixing valves, or pumps. The type of mixing device and degree of mixing are dependent on the feedstock, based on the flow properties of the feedstock and miscibility with water. The high-pressure mixed stream 152 can be heated further in a feed-effluent heat exchanger 154 to form a heated stream 156, which is then fed into a hydrothermal reactor 158. It can be appreciated that the feed-effluent heat exchanger 154 can be any combination of heat exchangers configured throughout the process to maximize overall thermal efficiency.

The hydrothermal reactor 158 creates turbulent fluid dynamics and achieves higher operating temperatures than the prior art systems for desalting (less than 100° C.) or fat-splitting (250-260° C.), such as operating temperatures at 300° C.-500° C. At these high temperatures, the hydrothermal reactor 158 achieves high rates of solvation and hydrolysis, which greatly reduces residence time and reactor size relative to prior art systems. The operating conditions of the hydrothermal reactor 158 may be selected based on the constituents of the feedstock and the desired cleanup requirements. The water-to-oil weight ratio in the hydrothermal reactor 158 may be between 1:100 and 3:1, such as between 1:10 and 1:1. The hydrothermal reactor 158 is operated at high pressure to maintain liquid, vapor-liquid, or supercritical phases such as in the range of 500-6,000 psig or 2,000-3,500 psig. The hydrothermal reactor 158 is configured to achieve and operate at turbulent flow conditions to optimize mixing and maximize heat transfer. At operating conditions, superficial residence times range from less than 10 seconds to 15 minutes depending on feedstock and cleanup goals. As used herein, superficial residence time is calculated based on the reactor volume and the volume of the feedstocks at standard conditions (temperature of 20° C. and pressure of one atmosphere). Actual hydraulic residence times may be calculated based on operating conditions (temperature and pressure) and the water-to-oil weight ratio. The hydrothermal reactor 158 can be a tubular plug-flow reactor (PFR), continuous stirred-tank reactor (CSTR), or any combination of these reactor types, such as PFR followed by CSTR, CSTR followed by PFR, or PFR followed by CSTR followed by PFR. Different reactor configurations provide a range of mixing, heat transfer, residence time, and product quality scenarios suited for feedstock type of cleanup objectives. For instance, cleanup requiring relatively low pressure (less than 1,000 psig), low temperature (less than 300° C.), liquid-phase operation, and long residence time may be effectively performed in CSTR-type HCU reactors. Cleanup requiring higher temperature and pressure or short residence time may be more effectively performed in PFR-type HCU reactors. In general, PFR systems will exhibit a Reynold Number (Re) of at least 2,000, such as 2,000-4,000, resulting in turbulent flow, high-heat transfer rate, and intimate mixing. The present invention employs a combination of residence times less than 15 minutes and Reynold Number (Re) greater than 4,000 throughout the HCU reaction zone. One example of a hydrothermal reactor 158 that can be used is the high-rate reactor disclosed in U.S. Patent Application Publication No. 2014/0109465, the disclosure of which is incorporated herein in its entirety.

Such a high-rate reactor may be used to convert petroleum-based oils and renewable feedstocks into lower molecular weight compounds suitable for distillate fuels or chemicals by achieving cracking and cyclization reactions (conversion) in supercritical water at conditions necessary for conversion, such as at temperatures greater than 450° C. At the conditions required to achieve these conversion reactions, contaminants in the feedstock such as inorganic impurities and asphaltenes lead to the formation of coke reactor fouling and affect performance. In contrast, the HCU reactor of the present invention removes those contaminants that would otherwise affect the performance of a high-rate conversion reactor.

Therefore, the HCU reactor is operated at conditions (such as temperatures below 450° C.) where conversion reactions do not typically occur and where coke that would affect performance is not readily formed. Instead, inorganic and heavy organic contaminants are liberated at HCU operating conditions and removed by the integrated HCU reactor and vapor-liquid separation systems. The HCU reactor may be operated in liquid, vapor, or supercritical modes, whereas a high-rate conversion reactor is operated at or near supercritical water conditions and the purpose is not to effect separation but to achieve chemical conversion reactions.

Liquid phase operation is desirable when contaminants of interest partition into liquid water more efficiently than into supercritical water or vapor phase. Conversely, supercritical phase operation is desirable when contaminants of interest are not soluble in supercritical water and separate from clean oil more efficiently than in liquid or vapor-phase modes. Vapor-phase mode facilitates operation at lower pressures (500-1,000 psig), higher temperatures (350-450° C.), and higher energy, which may be necessary for optimal separation of clean oil from contaminants in the integral vapor-liquid separation system. The water used in high-rate conversion reactions serves as a reaction catalyst. In the present invention, water does not serve as a catalyst; it is used for hydrolysis (such as of triglycerides) and as a carrier for separation or segregation of the contaminants from the feedstock.

Effluent 160 of the hydrothermal reactor 158 is cooled in the feed-effluent heat exchanger 154, yielding a partially-cooled product 162, which then passes through a pressure control valve 164 that maintains system pressure. Depressurized product stream 166 is further cooled as necessary by a cooling heat exchanger 168. A cooled product stream 170 is then fed to an oil-water separator 172. Clean oil 174 and process water stream 176 are removed from the separator 172. The HCU system 110 operated as described above rapidly dissociates inorganic contaminants (e.g., salts, minerals, and/or metals) which partition into the process water stream 176 and greater than 95% (such as at least up to 99%) of the contaminants are eliminated from the contaminated feedstock 112.

The clean oil 174 may be further processed (not shown) into chemicals or fuels depending on the type of feedstocks treated and the product objectives. Renewable and petroleum feedstocks may be hydrothermally cracked into synthetic crude via a high-rate hydrothermal reactor system (as described above) and then hydrotreated into transportation fuels or chemicals. Alternatively, renewable oil product may be converted into biodiesel via esterification or hydrotreatment, hydroisomerization, and hydrocracking into renewable fuels and chemicals via conventional refining processes.

The process water stream 176 may be treated and reused, further processed to recover byproducts, applied to land, or treated in conventional wastewater treatment processes and eliminated (not shown). The fate of the process water stream 176 is dependent at least in part on the constituents of the feedstock and the byproduct recovery objectives. For instance, when the HCU system 110 is used for desalting the feedstock, the process water stream 176 may contain both inorganic and trace organic contaminants and may be sent directly to wastewater treatment. The contaminants in clean oil 174 from petroleum-based feedstock may be reduced to less than 0.2% carbon residue, less than 0.1% asphaltene, less than 0.05% ash, and less than 20 ppm metals total.

The system 110 depicted in FIG. 1 may be used for rapid hydrolysis. Rapid hydrolysis is most effectively accomplished in a liquid or hydrothermal operation. During rapid hydrolysis of triglyceride oils, the clean oil 174 includes FFAs and the process water stream 176 includes water and glycerin. Pure glycerin can be recovered from the process water stream 176 by conventional distillation processes.

Alternatively, system 110 may be used for degumming or phosphorus removal. Rapid phosphorus removal is most effectively accomplished in the liquid phase where the temperature and pressure are controlled to maintain water in the saturated phase. Rapid hydrolysis of phospholipids in hydrothermal reactor 158 is achieved by cleaving the phosphate group from the glycerin backbone of a phospholipid as well as cleaving groups that may include fatty acids and other organic constituents from the phospholipid such as choline, ethanolamine, serine, or inositol constituents of phospholipids undergoing HCU. Phosphate is removed in the aqueous phase of the reaction mixture, while the fatty acids, which typically represent over 70 wt % of a phospholipid, are retained for subsequent processing into chemicals or fuels. The phosphorus content of clean oil 174 from the feedstock high in phospholipid content may be reduced from greater than 1,000 ppm to less than 50 ppm and metal content may be reduced to less than 20 ppm total. The yield of low-phosphorus oil from oil high in phospholipids is greatly increased compared to conventional degumming processes. For example, for an algal oil containing 6,000 ppm of phosphorus, the HCU process may increase the yield of low-phosphorus oil by more than 10%, whereby the clean oil 174 includes clean FFAs with a phosphorus content of less than 50 ppm. The process water stream 176 includes water and phosphate ion ($PO_4^{3-}$) and may be recovered and reused as a nutrient source for growing crops or algae.

Figure 2:
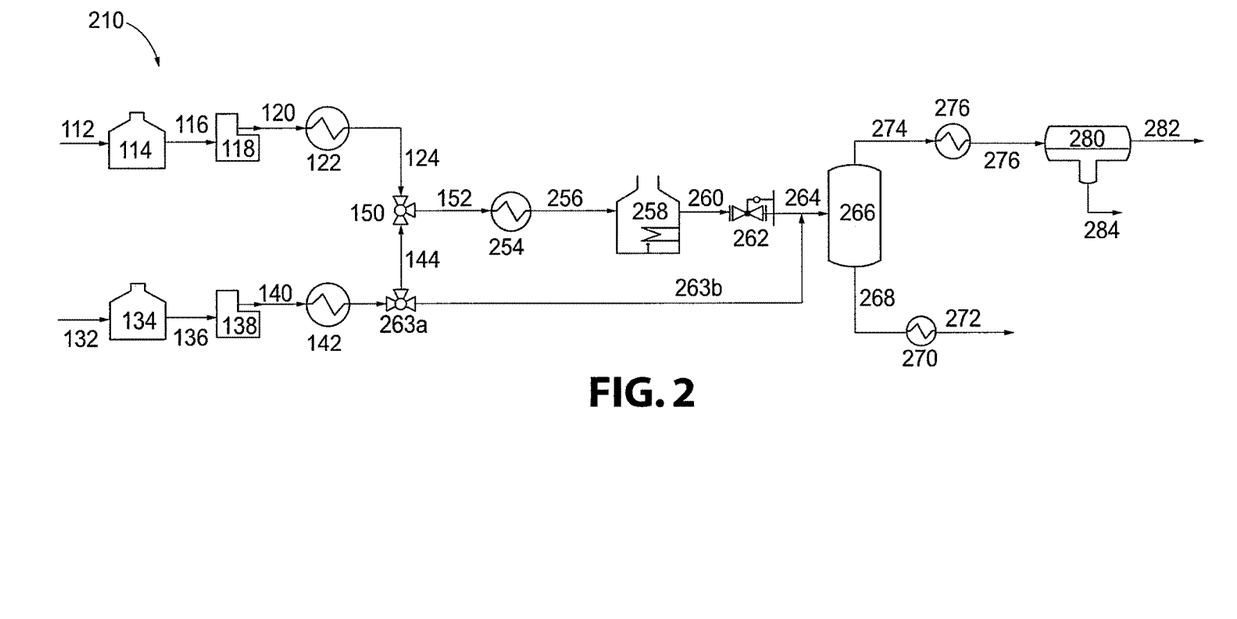
FIG. 2 is a schematic view of the HCU system in accordance with the invention for renewable oils or petroleum-based oils that incorporates a vapor-liquid separator for the separation and recovery of clean renewable or petroleum oil and residual oil.

Reference is now made to FIG. 2, which shows a schematic view of an HCU system 210 that incorporates a system for the separation and recovery of FFAs, clean petroleum fractions, or other hydrocarbon products. This system is similar to the embodiment shown in FIG. 1, but is configured with vapor liquid separation system to facilitate separation and recovery of clean oil and concentrate residual stream containing contaminants. The system 210 includes a feed system as shown in FIG. 1 for providing a contaminated feedstock 112, fed into an equalization tank 114, feedstock 116 exiting the equalization tank 114, and entering into pump 118 to form a pressurized feed stream 120, which can be heated by a heating device, such as a heat exchanger 122, to form a heated feed stream 124. Water feed stream 132 may be supplied to an equalization tank 134, fed at 136 to a pump 138, with pressurized water stream 140 heated by a heating device, such as heat exchanger 142, to form a heated water stream 144 that is mixed at mixing device 150 with the pressurized water stream 140 to form a high-pressure mixed stream 152. The high-pressure mixed stream 152 can be heated further in a feed-effluent heat exchanger 254 to form a heated stream 256, which is then fed into the hydrothermal reactor 258. It can be appreciated that the feed-effluent heat exchanger 254 can be any combination of heat exchangers configured throughout the process to maximize overall thermal efficiency. Hydrothermal reactor 258 may be operated within the same range of process conditions as hydrothermal reactor 158 (e.g. 300-500° C., 500-6,000 psig, superficial residence time less than 15 minutes, turbulent flow, and water-to-oil feed ratio of 1:100-3:1), but this is not meant to be limiting. For example, when the separation processes in the system 210 of FIG. 2 are operated in the vapor phase or supercritical conditions, the reactor conditions are adjusted accordingly.

Effluent 260 of hydrothermal reactor 258 is then passed through a pressure control valve 262 that maintains system pressure. A depressurized product stream 264 is fed to a vapor-liquid separation system 266 that is appropriately configured to meet product separation objectives. It can be appreciated that the separation system 266 may be comprised of one or more vapor-liquid separation unit operations including single-stage flash, rectification, stripping, or distillation where the configuration and operation are dependent on the feedstock and product cleanup requirements. If the feedstock and HCU reactor conditions result in high volatility of the clean oil product, or if high water ratio (over 10%) is employed, then a simple flash separation system may be used. For more stringent product purity or product exhibiting a distillation end point greater than 350° C., a rectification, stripping, or distillation column may be required. For example, the vapor-liquid separation system 266 may be operable at pressures of 2-50 psig and temperatures less than 250° C. to recover clean oil with a distillation endpoint less than 350° C. Alternatively, the vapor-liquid separation system may be operated at temperatures over 400° C. to recover clean oil product with distillation end points greater than 500° C. In addition, system 210 may optionally include addition of a portion of the water to depressurize product stream 264 via valve 263a at a line 263b, thereby providing an option for improving the yield and quality of the product stream 274. The bottoms product 268 from the vapor-liquid separation system 266 is cooled to less than 150-200° C., typically in less than 5 seconds in a combination heat exchanger 270 and direct contact quench system, to produce a residual product 272. The residual product 272 may be further converted to hydrogen, fuel gas, distillate products, and coke by conventional coking and gasification processes, or may be used directly, for example, as an asphalt blending component.

The overhead fraction 274 from the vapor-liquid separation system 266 is condensed in heat exchanger 276. The condensed product is separated in an oil-water separator 280 at near ambient pressure and at 30-100° C. depending on feed stock, product volatility, and product separation objectives. A clean oil stream 282 and a water stream 284 are recovered from oil-water separator 280. The clean oil stream 282 may be further processed into chemicals or fuels (not shown). For example, the clean oil stream 282 may be hydrothermally cracked into synthetic crude via another hydrothermal reactor system and then hydrotreated into transportation fuels or chemicals. Alternatively, renewable clean oil FFAs may be converted into biodiesel via esterification or hydrotreated, hydroisomerized, and hydrocracked into renewable fuels and chemicals via conventional refining processes.

The hydrothermal cleanup system 210 of FIG. 2 may be operated in a manner to achieve rapid hydrolysis and cleanup of waste renewable oils such as yellow and brown grease. Yellow grease may consist of used or waste vegetable oils and can also include certain grades of tallow from rendering processes. Yellow grease is typically specified as containing no more than 15% FFAs. Brown grease is a generic term that may include trap grease and grease from sewage treatment plants. Brown grease typically includes 50-100% free fatty acids. Brown grease may contain several thousand ppm of metals and several percent of insoluble impurities. Therefore, brown grease, which is a very low-cost commodity relative to yellow grease or virgin plant oils, is typically not an acceptable feedstock for the production of biodiesel or renewable diesel without extensive pretreatment.

Figure 3:
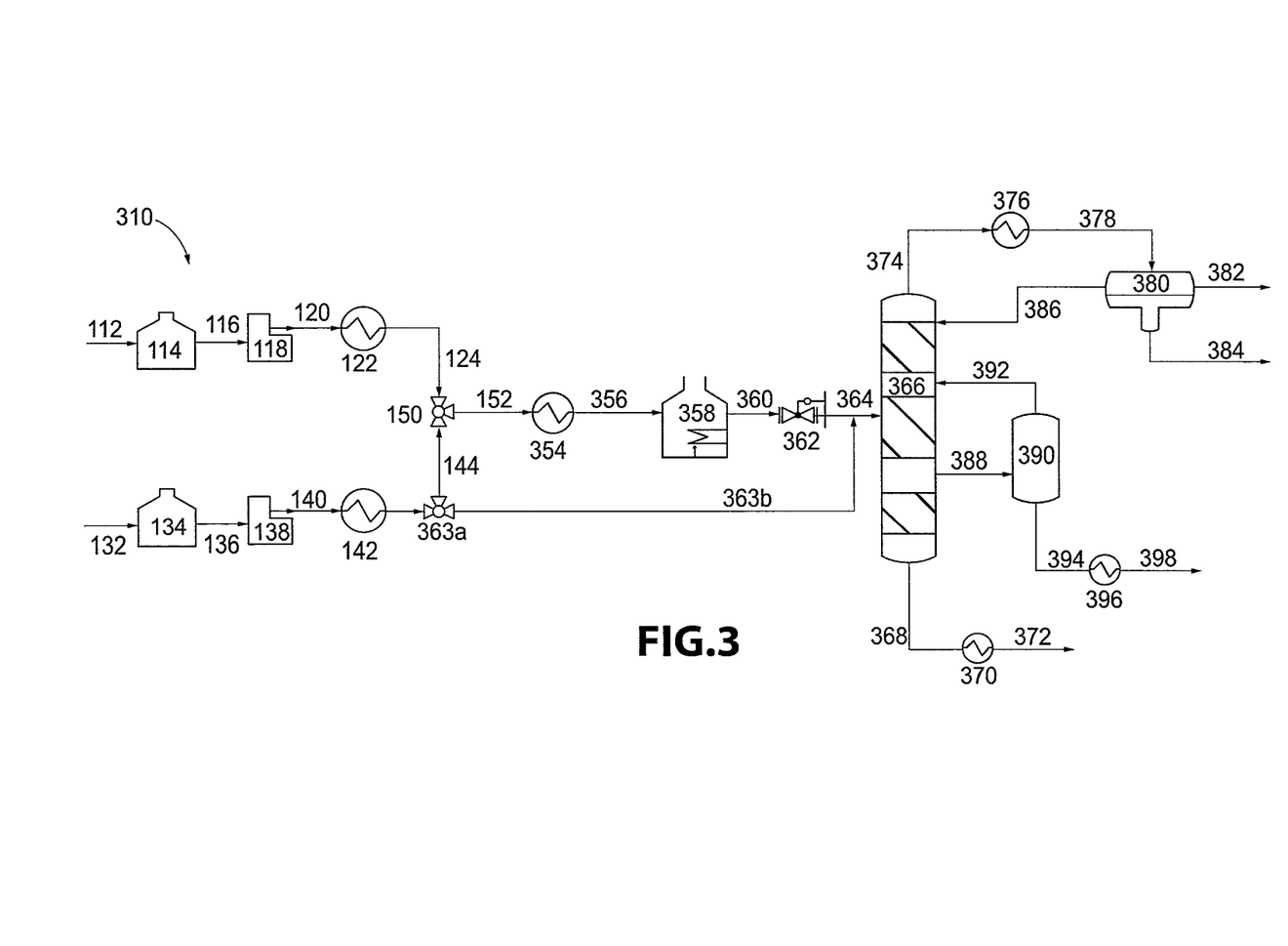
FIG. 3 is a schematic view of the HCU system in accordance with the invention for renewable oils or petroleum-based oils that includes a rectifying column for the separation and recovery of short- and long-chain FFA fractions or petroleum fractions.

Reference is now made to FIG. 3, which is a schematic view of an HCU system 310 for processing renewable or petroleum feedstocks that further incorporates a distillation system for the separation and recovery of short- and long-chain free fatty acids or petroleum distillate fractions. The water and oil feed components depicted in FIG. 3 are identical or similar to those depicted in FIGS. 1 and 2. The high-pressure mixed stream 152 can be heated further in a feed-effluent heat exchanger 354 to form a heated stream 356, which is then fed into the hydrothermal reactor 358. It can be appreciated that the feed-effluent heat exchanger 354 can be any combination of heat exchangers configured throughout the process to maximize overall thermal efficiency. The reaction temperature (350-450° C.) and water-to-oil ratio (0.1:1 to 2:1) for the hydrothermal reactor 358 in HCU system 310 are controlled to effect hydrolysis, degumming, and other cleanup reactions in addition to providing sufficient energy for downstream separation operations. One feature of system 310 is the ability to take advantage of the energy of the HCU product 360 to perform product separation in an integrated system without product decomposition or the need for additional energy input as would be required using a reboiler or the like. The vapor-liquid separation is configured in such a manner to use the thermal energy and water present in the hydrothermal reactor effluent to effect separation and concentration of FFAs from renewable oils; or separation of petroleum oils into petroleum fractions such as naphtha, diesel, or vacuum gas oil (VGO) equivalent. In addition, the separation system in system 310 operates at near atmospheric pressure and does not require a vacuum due to the high operating temperature (350-450° C.) and the manner in which water is employed in the HCU process. The hydrothermal reactor 358 may be operated at higher temperatures (over 350° C.) than typical atmospheric distillation processes because the water, in saturated liquid, steam, or supercritical phases, inhibits thermal degradation of the feedstock. Higher temperature operation imparts more energy to the separation process and increases the vapor pressure of the oil components. After pressure letdown at pressure control valve 362, the water, which is flashed to the vapor phase, has the effect of further reducing the partial pressure of the organic constituents. The reduced vapor pressure of the high-boiling constituents improves mass transfer from the liquid to the vapor phase. The combined effect of these two factors permits recovery of organic constituents with normal boiling point greater than 550° C.

The depressurized product stream 364 is fed directly to a separation system 366 configured to separate short-chain and long-chain fatty acids or to separate petroleum distillate fractions. The separation system 366 may consist of stripping, rectification, or distillation operations. For example, system 310 may also optionally include a valve 363a and line 363b for delivery of a portion of the water to depressurized product stream 364 for improving the yield and quality of the product stream 374. As used herein, short-chain fatty acids have up to 12, 14, 16, or 18 carbon atoms (C12, C14, C16, or C18) and long-chain fatty acids have at least 18, 20, or 22 carbon atoms (C18, C20, or C22), noting that there is some overlap therebetween, depending on operating conditions. Since FFA volatility is, in general, inversely proportional to fatty acid chain length, short-chain fatty acids that are more volatile may be separated from long-chain fatty acids that are less volatile. The more volatile, overhead fraction 374 may include fatty acid fractions up to C12, C14, C16, or C18 depending on operating conditions of the hydrothermal reactor 358. The less volatile fraction may include fatty acid fractions heavier than C16, C18, C20, or C22.

An overhead fraction 374 from the separation system 366 is fed to an overhead condenser 376. A resulting cooled overhead product 378 enters an oil-water separator 380 where a fraction of the short-chain FFAs may be returned at 386 to the separation system 366 to provide reflux and the remainder of the short-chain FFAs are produced at 382 as product. By controlling the reflux ratio (0.1 to 10), in addition to water-to-oil feed ratio (0.1:1 to 2:1) and hydrothermal reactor 358 operating conditions (350-450° C.), performance of the separation system 366 can be optimized to effect the desired separation of short- and long-chain fatty acids. The short-chain FFA product 382 may be further processed into chemicals or fuels (not shown) or the short-chain FFA product 382 may be hydrothermally cracked into synthetic crude via another high-rate hydrothermal reactor system and then hydrotreated into transportation fuels or chemicals. Alternatively, short-chain FFAs may be converted into biodiesel via esterification, or hydrotreated, hydroisomerized, and hydrocracked into renewable fuels and chemicals via conventional refining processes. Product water 384 may be recovered and reused, with or without treatment depending on feedstock quality and HCU product quality requirements.

Long-chain FFAs are recovered in a bottom stream 368 from separation system 366. The long-chain FFAs in bottom stream 368 are then cooled in a bottoms product heat exchanger 370 to produce a cooled long-chain FFA product stream 372. The long-chain FFA product stream 372 may be further processed into chemicals or fuels (not shown). The long-chain FFAs may be hydrothermally cracked into synthetic crude and then hydrotreated into transportation fuels or chemicals. Alternatively, the long-chain FFAs at 372 may be converted into biodiesel via esterification, or hydrotreated, hydroisomerized, and hydrocracked into renewable fuels and chemicals via conventional refining processes.

The separation system 366 may be configured to concentrate and recover specific FFAs or distillate fractions by including a separator side stream 388 and the inclusion of a stripping vessel 390. For instance, the separator side stream 388 may be used to recover concentrated C18, C20, C22, or C24 FFAs from a triglyceride or FAA feedstock that contains a mixture of FAA ranging from C12 through C24 or higher. A reflux stream 392 may be used to control product purity. Reflux at stream 392 improves the efficiency of the separation system 366 by returning a portion of the liquid product to the separation system 366, which cools and condenses upflowing vapors. The net effect is a reduction in the number of theoretical stages of separation required in the column. By selecting the location for withdrawal of separator side stream 388 and return of reflux stream 392, the concentration of a particular FFA, such as C22, can be maximized. A purified product stream 394 may be cooled in heat exchanger 396 resulting in cooled product 398. Withdrawing a side stream in separation system 366 produces a clean, heavy distillate fraction at cooled product 398. The bottom stream 368, is rapidly cooled in heat exchanger 370 to produce a product stream 372 that contains inorganic and heavy organic contaminants such as asphaltenes.

System 310 may also be used to cleanup petroleum crude oil, ATBs, or vacuum tower bottoms (VTB). When processing a petroleum crude oil, operating conditions may be controlled to product a light distillate at 382, heavy distillate at 398, and residual fraction at 372. The light distillate 382 may include naphtha or naphtha and diesel fractions. The heavy distillate 398 may include diesel or vacuum gas oil (VGO) equivalent, or both diesel and VGO equivalent fractions. Undesirable contaminants including metals, asphaltenes, and precursors to Conradson Carbon Residue (CCR) formation are concentrated in the residual product 372.

An advantage of the HCU process and system of the present invention is that the small physical footprint of the systems 110, 210, and 310 requires low capital and operating costs. The HCU process can operate at very short residence times, such as less than two minutes. This results in relatively small equipment and low capital cost. Atmospheric pressure operation (instead of vacuum operation) further reduces the physical footprint, operating cost and capital cost. When used for degumming, operating costs for the HCU are lower than conventional chemical degumming because degumming acids are not required, products and byproducts are easily separated and recovered using conventional oil-water separation technology, high-quality water may be recovered and reused without additional treatment, other valuable byproducts, such as glycerin, may be recovered, and no other waste products are generated.

It should be appreciated that optimal cleanup conditions are dependent on feedstock quality and operating conditions can be varied to achieve the desired product quality. For example, when processing renewable oils, operating conditions can be varied to maximize desalting (e.g., waste vegetable oil) or maximize glycerin recovery. It can also be appreciated that the HCU process may be operated in a manner to cleanup highly contaminated feedstocks, such as brown grease, and produce a clean overhead product and a bottoms byproduct that contains inorganic contaminants.

The following Examples are presented to demonstrate the general principles of the invention. All amounts listed are described in parts by weight, unless otherwise indicated. The invention should not be considered as limited to the specific Examples presented. Whereas particular embodiments of this invention have been described above for purposes of illustration, it will be evident to those skilled in the art that numerous variations of the details of the present invention may be made without departing from the invention as defined in the appended claims.

EXAMPLES

Example 1

HCU Rapid Hydrolysis

Unrefined soybean oil was used as the feedstock to a pilot scale HCU system configured as shown in FIG. 1 to conduct rapid hydrolysis at temperatures greater than 290° C. without glycerin decomposition. Actual operating conditions are provided in Table 1 with reactor temperature of 340° C. and reactor pressure controlled at 2,500 psig to maintain the reaction mixture in the liquid phase. At these conditions, the triglyceride feedstock, water, and products of hydrolysis (glycerin and free fatty acids) are miscible. The very short residence time in liquid phase, and relatively low concentration of glycerin, resulted in near complete hydrolysis and inhibited glycerin decomposition. Upon cooling via the feed-effluent heat exchanger and product cooler, an organic phase containing FFAs and an aqueous phase containing glycerin and water were separated in an oil-water separator.

TABLE 1

HCU Operating Conditions for Rapid Hydrolysis

| Parameter | Value |
|---|---|
| Soybean oil flow rate, mL/min | 40 |
| Water flow rate, mL/min | 20 |
| Total flow rate, mL/min | 60 |
| Water fraction of total feed, % | 33 |
| Reactor temperature, ° C. | 340 |
| Reactor pressure, psig | 2,500 |
| Superficial residence time, min | 17.8 |
| Actual hydraulic residence time, min(approx.) | 11.2 |
| Reactor Reynolds Number, Re | >4,000 |
| Gas generation, $ft^3$/bbl | Negligible |

The same feedstock was hydrolyzed in a 1-liter Parr reactor, operated as a CSTR batch process, to produce completely hydrolyzed product for comparison to HCU hydrolyzed product. A summary of operating conditions and product yields is provided in Table 2.

TABLE 2

Summary of HCU Rapid Hydrolysis Results

| Parameter | Soybean oil | Batch hydrolysis | HCU hydrolysis |
|---|---|---|---|
| Temperature, ° C. | | 280 | 340 |
| Pressure, psig | | 915 | 2,500 |
| Residence time, min | | 180 | 11.2 |
| FFA total acid number, mg KOH/g | 1 | 170 | 172 |
| Glycerin yield, % of theoretical | | 62 | 76 |
| FFA yield, % of theoretical | | 98.6 | 93.5 |
| FAA composition, % of total FFA of fatty acids (by FAA type - number carbon atoms to number double bonds) | | | |
| 14:0 | | | 0.1 |
| 16:0 | 11.8 | 12.3 | 12.3 |
| 16:1 | | | 0.1 |
| 18:0 | 4 | 5.6 | 5.4 |
| 18:1 | 13.5 | 14.7 | 14.4 |
| 18:2 | 64.5 | 62.8 | 60.2 |
| 18:3 | 5.2 | 0.4 | 0.2 |
| >18 | 1 | 2.3 | 3.3 |
| Other/unidentified | | 1.9 | 2.6 |

The total acid number of the resultant FFA phase for both batch and HCU hydrolysis were similar and near a theoretical value of 186 for this feedstock, indicating near complete hydrolysis was achieved in both cases. High glycerin recovery was also achieved. Glycerin losses may include glycerin that partitioned to the organic, FFA phase, and unhydrolyzed mono- or diglycerides. A high yield of FFAs was also achieved. However, it is interesting to note that gamma-linolenic acid (18:3), and to a lesser extent linoleic acid (18:2), was lost due to isomerization or other reactions. Loss of 18:3 occurred even at the batch conversion temperature, 280° C. The most important result is that hydrolysis performance similar to the Colgate-Emery process can be achieved in less than one tenth of the time, which reduces equipment size by a factor of ten and greatly reduces capital cost.

Example 2

Hydrothermal Cleanup of Yellow and Brown Grease

A pilot HCU system was configured as shown in FIG. 2. The vapor-liquid separation system was a flash drum modified with internal packing to aid in demisting the vapor product. No external reflux was provided for rectification of the overhead product. The feedstock consisted of a 60:40 blend of yellow grease (YG) and brown grease (BG). The brown grease acquired for this example had been dewatered and filtered. The feedstocks were desalted using a simple water wash and blended before processing by HCU. A summary of HCU operating conditions for this example is provided in Table 3.

TABLE 3

Summary of HCU Operating Conditions for Waste Oil Cleanup

| Parameter | Value |
| --- | --- |
| 60:40 YG:BG flow rate, mL/min | 135 |
| Specific gravity of 60:40 YG:BG blend, g/cc | 0.948 |
| Water flow rate, mL/min | 135 |
| Total flow rate, mL/min | 270 |
| Water fraction of total feed, vol % | 50 |
| Reactor temperature, ° C. | 450 |
| Reactor pressure, psig | 500 |
| Superficial residence time, sec | 120 |
| Actual hydraulic residence time, sec (approx.) | ≤5 |
| Reactor Reynolds Number, Re | >40,000 |
| Gas generation, ft$^3$/bbl | negligible |

In this example, HCU reactor temperature and pressure were controlled to result in a vapor-phase reaction. At these conditions, rapid hydrolysis was achieved and inorganic constituents were liberated and not vaporized, but concentrated in effluent stream. At the operating conditions employed in this example, the actual hydraulic residence time of the mixed feed stream was calculated as less than or equal to 5 seconds. While complete hydrolysis was achieved at these conditions, the temperature and the partial pressure of FFAs in water vapor prevented significant deterioration of the oil product.

Table 4 provides a summary of waste oil cleanup results. Very little product decomposition was noted based on a high yield of clean oil (94.9%), FFA composition of the clean oil (94.2%), and lack of significant gas generation. The yield loss was 2.3%. This loss was due to organic constituents dissolved in the product water stream. These organic constituents include low molecular weight carboxylic acids, glycerin, and glycerin decomposition products. Elemental analysis of the water product showed that it contained 1.78 wt % carbon. Near complete hydrolysis was observed as demonstrated by the very low concentration (less than 1 wt %) of mono-, di-, and triglycerides in the product and correspondingly high concentration of FFAs. Near complete metal reduction was also obtained with most results below the reporting limit of 0.1 ppm. The phosphorus balance was near 100%. However, complete recovery of divalent species was not obtained. Most of the loss was associated with the formation of soaps or similar materials that were entrained with the overhead product and partitioned into the aqueous phase. For instance, only about 20% of the calcium present in the feed was accounted for in the HCU clean product and residual product. The calcium concentration in the aqueous product was 83 ppm which represents the balance of the calcium that was in the form of soaps or salts in aqueous solution.

TABLE 4

Summary of Waste Oil Cleanup Results

| Parameter | HCU feed | HCU clean product | HCU Residual |
| --- | --- | --- | --- |
| Yield, wt % | 100 | 94.9 | 2.8 |
| Component type, wt % | | | |
| Low molecular weight compounds | 1.1 | 4.8 | |
| Free fatty acids | 45.9 | 94.2 | |
| Monoglycerides | 0.2 | 0.8 | |

TABLE 4-continued

Summary of Waste Oil Cleanup Results

| Parameter | HCU feed | HCU clean product | HCU Residual |
| --- | --- | --- | --- |
| Diglycerides | 12.5 | 0.2 | |
| Triglycerides | 40.1 | <0.1 | |
| Metals analysis, wt ppm | | | |
| P | 0.86 | <0.1 | 17.2 |
| Ba | <0.1 | <0.1 | 0.3 |
| Ca | 133 | 19.8 | 288 |
| Cu | 0.44 | <0.1 | 15.7 |
| Mg | 0.3 | <0.1 | 1.8 |
| Zn | 1.1 | 0.5 | 9.3 |

Example 3

Phospholipid Cleanup

A feedstock that is high in phospholipid content and other inorganic contaminants was processed. This feedstock was comprised of partially refined microbial oils and plant oils that contained a broad mixture of lipid types including triglycerides, phospholipids, alcohols, and long chain waxy esters. At HCU operating conditions, phospholipid molecules and triglycerides are rapidly hydrolyzed as demonstrated in Example 1. Phosphorus from the phospholipids is mostly liberated as phosphate ion ($PO_4^{3-}$).

In this example rapid hydrolysis was performed in the HCU system configured as shown in FIG. 1. The HCU reactor was controlled at 2,500 psig and 340° C. to maintain the reaction mixture in the liquid phase. Table 5 provides a summary of the operating conditions. At these conditions, the feedstock, water, and products of hydrolysis (glycerin, FFAs, and inorganics) are miscible. Upon cooling via a feed-effluent heat exchanger and cooling heat exchanger, an organic phase consisting of FFAs and other hydrocarbons, and an aqueous phase containing phosphate, glycerin, and water, readily separated in an oil-water separator.

TABLE 5

Summary of HCU Operating Conditions for Phospholipid Cleanup

| Parameter | Value |
| --- | --- |
| High phospholipid oil flow rate, mL/min | 40 |
| Water flow rate, mL/min | 20 |
| Total flow rate, mL/min | 60 |
| Water fraction of total feed, vol % | 33 |
| Reactor temperature, ° C. | 340 |
| Reactor pressure, psig | 2,500 |
| Superficial residence time, min | 10.5 |
| Actual hydraulic residence time, min (approx.) | 6.5 |
| Reactor Reynolds Number, Re | >5,000 |
| Gas generation, ft$^3$/bbl | negligible |

Table 6 provides a summary of the phospholipid oil cleanup results. Very little product decomposition was noted based on negligible gas generation and total product recovery of 99 wt %. Near complete hydrolysis was observed as demonstrated by the complete conversion of triglycerides and correspondingly high concentration of FFAs and glycerin. Based on gas chromatographic analysis, mono- and diglyceride values may include other organic constituents, such as hydrocarbons and alcohols, and likely do not accurately reflect only just the mono- and diglyceride fraction.

Greater than 99% of the phosphorus was removed from the feedstock. 86% of the phosphorus was recovered as phosphate ion ($PO_4^{3-}$) in the aqueous phase as measured by ion chromatography. The remaining phosphorus formed insoluble salt complexes with magnesium, zinc, and calcium, which accounts for the low recovery (20-40%) of these ions in the aqueous phase. The very high ash reduction (over 98%) also indicates near completed removal of inorganic constituents from the organic product.

TABLE 6

Summary of Phospholipid Oil Cleanup Results

| Parameter | HCU Organic Feed | HCU Organic Product | HCU Aqueous Product |
|---|---|---|---|
| Feed streams, wt % | | | |
| Organic | 100 | 94.9 | |
| Water | | | 61.8 |
| Component type, wt % | | | |
| Free fatty acids | 0.7 | 93 | |
| Mono glycerides | 8.4 | 5.3 | |
| Di glycerides | 11.0 | 1.8 | |
| Tri glycerides | 80.0 | 0.0 | |
| Glycerin | | | 12.0 |
| Metals analysis, wt ppm | | | |
| P | 1,800 | 15 | 2,500 |
| K | 160 | | 490 |
| Na | 294 | | 370 |
| Ca | 16 | | 5 |
| Si | 57 | | |
| Fe | 36 | | |
| Mg | 164 | | 48 |
| Zn | 10 | | 6 |
| Ash, wt % | 0.60 | 0.01 | |

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of this description. For example, it is to be understood that the present invention contemplates that, to the extent possible, one or more features of any embodiment can be combined with one or more features of any other embodiment.

Whereas particular embodiments of this invention have been described above for purposes of illustration, it will be evident to those skilled in the art that numerous variations of the details of the present invention may be made without departing from the invention as defined in the appended claims.

The invention claimed is:
1. A process for reducing contaminants in petroleum or renewable feedstocks comprising:
   combining a feedstock comprising contaminants with a water feed to form a contaminated feedstock-water mixture;
   feeding the mixture into a hydrothermal reactor, wherein the mixture is subject to heat, pressure, and turbulent flow conditions that do not cause conversion of the feedstock, wherein the turbulent flow in the hydrothermal reactor has a Reynolds Number (Re) of at least 2000;
   maintaining the temperature, pressure, and turbulent flow conditions of the mixture such that inorganic contaminants are liberated from the feedstock in the mixture without feedstock conversion; and
   separating an effluent of the reactor into an aqueous stream and at least one product stream having inorganic contaminants at a lower concentration than in the contaminated feedstock.

2. The process of claim 1, wherein the feedstock is a petroleum-based feedstock selected from the group consisting of petroleum crude oil, shale oil, petroleum refinery intermediate streams including atmospheric tower bottoms (ATB) and vacuum tower bottoms (VTB), pyrolysis oils, recycled plastic, coal liquids, used motor oil, and mixtures thereof.

3. The process of claim 1, wherein the feedstock is a renewable feedstock comprised of plant oils selected from the group consisting of canola, Carinata, castor, Jatropha, palm, Pongamia, soy bean, and/or corn; soap stock; waste vegetable oil; yellow grease; brown grease; acidic oils, animal tallow; algal oil; microbial oil; pine-related byproducts from tall oils; biosynthetic oil; and mixtures thereof.

4. The process of claim 3, wherein the plant oils comprise at least one of triglycerides, diglycerides, monoglycerides, and combinations thereof, and, wherein the product stream comprises free fatty acids and/or glycerin.

5. The process of claim 1, wherein the feedstock comprises a mixture of petroleum-based and renewable oils.

6. The process of claim 1, wherein the water and contaminated feedstock are mixed by combining the two streams using a tee connection, a static mixer, pump, or a mixing valve and the mixture is maintained in turbulent flow.

7. The process of claim 1, wherein water is added to the reactor effluent before separation into the aqueous stream and the at least one product stream to improve product yield or separation.

8. The process of claim 1, wherein the hydrothermal reactor comprises a tubular plug-flow reactor (PFR).

9. The process of claim 1, wherein the contaminated oil-water mixture is heated in the reactor to a temperature of 300° C.-500° C.

10. The process of claim 1, wherein the pressure in the hydrothermal reactor is maintained between 500 psig and 6,000 psig and is controlled to maintain the mixture in a liquid, vapor, or supercritical phase.

11. The process of claim 1, wherein the hydrothermal reactor is maintained at an operating pressure between 500 and 6,000 psig and an operating temperature between 300-500° C. and the feedstock is maintained in the reactor for a residence time of 5 seconds to 15 minutes.

12. The process of claim 1, wherein the feedstock is a renewable feedstock containing phospholipids and, wherein the phospholipids undergo hydrolysis of the phospholipid, cleavage of the phosphate group from the glycerin backbone, and/or cleavage of other organic constituents.

13. The process of claim 1, wherein the contaminants comprise inorganic contaminants comprising salts, metals, and/or minerals and/or organic contaminants comprising asphaltenes, high molecular weight polymers or waxes, coke, and/or coke precursors.

14. The process of claim 1, wherein the separating of the reactor effluent into the aqueous stream and the at least one product stream includes the steps of cooling, depressurizing, condensing, and separating to produce a clean oil stream comprising hydrocarbons and/or free fatty acids and a water stream comprising inorganic contaminants and/or glycerin.

15. The process of claim 1, wherein separating of the reactor effluent into the aqueous stream and the at least one product stream includes the steps of depressurizing the reactor effluent and expanding the reactor effluent in a vapor-liquid separation system operated at a pressure up to 50 psig.

16. The process of claim 15, wherein an overhead product from the vapor-liquid separation system is condensed and separated into a clean oil product and a water product.

17. The process of claim 15, wherein a bottoms product results from the vapor-liquid separation system which is comprised of residual product containing inorganic contaminants and/or asphaltene compounds.

18. The process of claim 15, wherein the vapor-liquid separation system is configured for one or more separation operations comprising flashing, rectification, stripping, distillation, condensing, and phase separation.

19. A hydrothermal cleanup system for decontaminating oils comprising:
   a hydrothermal reactor system operated at a temperature and pressure to maintain liquid, vapor-liquid, or supercritical conditions that result in hydrolysis and/or liberation of inorganic contaminants from a mixture of a feedstock oil and water without conversion of the feedstock, wherein the hydrothermal reactor system is operated at turbulent flow having a Reynolds Number (Re) of at least 2000; and
   a separation system for removing a clean product stream and water and/or oil stream containing inorganic contaminants from the effluent of the reactor system.

20. The system of claim 19, wherein the separation system is configured for one or more separation operations comprising flashing rectification, stripping, distillation, condensing, and phase separation.

\* \* \* \* \*

UNITED STATES PATENT AND TRADEMARK OFFICE
CERTIFICATE OF CORRECTION

PATENT NO. : 10,071,322 B2  
APPLICATION NO. : 15/007658  
DATED : September 11, 2018  
INVENTOR(S) : Edward N. Coppola et al.

Page 1 of 1

It is certified that error appears in the above-identified patent and that said Letters Patent is hereby corrected as shown below:

In the Claims

Column 20, Line 16, Claim 20, delete "flashing" and insert -- flashing, --

Signed and Sealed this  
Fourth Day of December, 2018

Andrei Iancu  
*Director of the United States Patent and Trademark Office*